United States Patent [19]

Felix

[11] 4,361,438
[45] Nov. 30, 1982

[54] SUBSTITUTED CYCLOPROPYL METHOXY PHENYL UREAS AND THE HERBICIDAL USE THEREOF

[75] Inventor: Raymond A. Felix, Richmond, Calif.

[73] Assignee: Stauffer Chemical Company, Westport, Conn.

[21] Appl. No.: 227,017

[22] Filed: Jan. 21, 1981

[51] Int. Cl.³ .................. A01N 9/20; C07C 103/19; C07C 103/127; C07C 103/133

[52] U.S. Cl. .................................. 71/98; 71/94; 71/105; 71/106; 71/111; 71/120; 260/465 D; 546/332; 560/32; 560/161; 560/163; 560/228; 560/255; 564/52

[58] Field of Search .............. 564/52; 71/120, 94, 71/98, 105, 111, 106; 260/465 D; 546/332; 560/32, 161, 163, 228, 255

[56] References Cited

U.S. PATENT DOCUMENTS

| | | | |
|---|---|---|---|
| 3,520,925 | 7/1970 | Koenig et al. | 564/52 X |
| 3,978,123 | 8/1976 | Chan | 71/120 X |
| 3,991,093 | 11/1976 | Koenig et al. | 71/120 X |
| 4,058,392 | 11/1977 | Thomas et al. | 564/52 X |
| 4,149,874 | 4/1979 | Felix | 564/52 X |

FOREIGN PATENT DOCUMENTS 2013669  8/1979  United Kingdom.

*Primary Examiner*—Thomas A. Waltz
*Attorney, Agent, or Firm*—Joel G. Ackerman

[57] ABSTRACT

Compounds having the formula

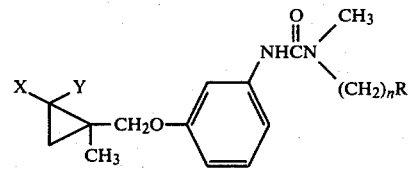

in which X and Y are halogen; R is cyano, halogen, thio-$C_1$-$C_4$ alkyl, phenyl, pyridyl, hydroxy, or $OR_1$; $R_1$ is $C_1$-$C_4$ alkyl, $C_1$-$C_4$ mono- or di-alkylcarbamyl, $C_2$-$C_6$ alkoxyalkyl, phenylcarbamyl, $C_1$-$C_6$ alkanoyl or $C_1$-$C_6$ haloalkanoyl; and n is: (a) 1 or 2 if R is thioalkyl, cyano or phenyl; and (b) 2 if R is otherwise as defined, are herbicides.

35 Claims, No Drawings

SUBSTITUTED CYCLOPROPYL METHOXY PHENYL UREAS AND THE HERBICIDAL USE THEREOF

This invention relates to novel herbicidal compounds having the formula

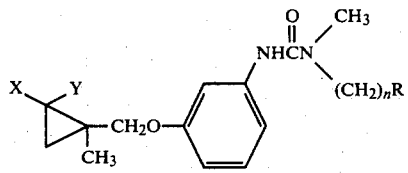

in which X and Y are halogen; R is cyano, halogen, thio-$C_1$-$C_4$ alkyl phenyl, pyridyl, hydroxy, or $OR_1$; $R_1$ is $C_1$-$C_4$ alkyl, $C_1$-$C_4$ mono- or di-alkylcarbamyl, $C_2$-$C_6$ alkoxyalkyl (preferably 1-alkoxyethyl), phenylcarbamyl, $C_1$-$C_6$ alkanoyl or $C_1$-$C_6$ haloalkanoyl; and n is: (a) 1 or 2 if R is thioalkyl, cyano or phenyl; and (b) 2 if R is otherwise as defined. As will be demonstrated by the data which follows, these compounds have been found to exhibit herbicidal properties.

The terms "halo" or "halogen" include fluoro, chloro, bromo, and iodo.

The compounds of this invention have been found to be active herbicides, in possessing herbicidal activity against various species of weeds. In the broadest sense, the term "weed" refers to plants which grow in locations in which they are not desired.

As will be seen from the data which follows, these compounds are basically inactive as pre-emergence herbicides, and are primarily active as post-emergence herbicides to control various broadleaf weeds.

This invention also relates to a method for controlling undesirable vegetation, particularly undesirable broadleaf vegetation, comprising applying to such vegetation a herbicidally effective amount of a compound as described herein, and also relates to herbicidal compositions of matter comprising a herbicidally effective amount of a compound as describd herein, together with an inert diluent or carrier suitable for use with herbicides.

As used herein, the term "herbicide" means a compound which controls or modifies the growth of plants, particularly of undesirable plants. By the term "herbicidally effective amount" is meant an amount of compound which causes a controlling or modifying effect on the growth of plants. The term "plants" is meant to include germinant seeds, emerging seedlings and established vegetation, including roots and above-ground portions. Such modifying and controlled effects include all deviations from natural development.

In general, the compounds of the present invention in which R is cyano, halogen, thioalkyl, phenyl, pyridyl or hydroxy, can be prepared by reacting an aromatic isocyanate with an appropriate amine:

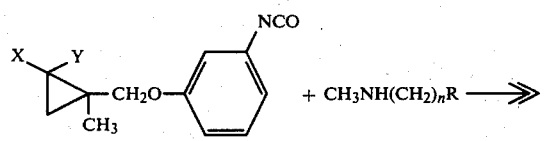

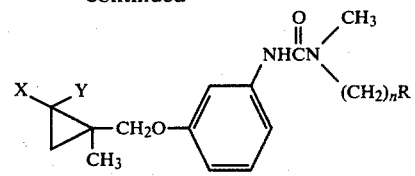

If the amine is used as the hydrochloride, a base such as triethylamine or an alkali metal salt must be employed. The reaction is conducted in an inert solvent such as methylene chloride, 1,2-dichloroethane, ether, toluene, acetone or acetonitrile, at a temperature of from about $-20°$ C. to about $100°$ C., preferably about $0°$ C.–$20°$ C. Reaction time may vary from as little as 5 minutes to as long as 12 hours. A small amount of triethylamine may be used as a catalyst. The isocyanate may be prepared by a two-step process from a hydroxyaniline, a cyclopropylmethyl halide, and phosgene, as described in U.S. Pat. No. 4,149,874.

Those compounds in which R is $OR_1$, may be prepared from compounds in which R is hydroxy ("alcohols") as follows:

(a) $R_1$ = alkyl- or phenylcarbamyl:

The alcohol is reacted with an isocyanate, similarly to the previous reaction of isocyanate and amine; under similar conditions.

(b) $R_1$ = alkanoyl or haloalkanoyl:

The alcohol is reacted with an appropriate acyl chloride in the presence of an added base such as triethylamine or pyridine, or in a two-phase system in the presence of an inorganic base such as sodium or potassium hydroxide, sodium carbonate or sodium bicarbonate, with an inert solvent, at temperatures of from about $-20°$ C. to about $+100°$ C.

(c) $R_1$ = alkoxyalkyl:

The alcohol is reacted with, for instance, a vinyl-lower alkyl ether, in an inert solvent such as diethyl ether, tetrahydrofuran, or methylene chloride, in the presence of an acid catalyst such as HCl, or methane- or toluenesulfonic acid, at a temperature of from about $-50°$ C. to about $+50°$ C.

(d) $R_1$ = alkyl:

The alcohol is alkylated according to conventional practices, for instance, with an appropriate alkyl halide.

The following are examples of the preparation of representative compounds according to the present invention.

EXAMPLE 1

Preparation of N-(2-hydroxyethyl)-N-methyl-N'-[3-(2,2-dichloro-1-methylcyclopropyl)methoxy]phenyl urea (Compound 1)

A solution of 1.63 g (0.022 mole) methylaminoethanol in 25 ml methylene chloride was prepared and cooled in an ice bath. Then, 5.98 g (0.022 mole) 3-(2',2'-dichloro-1'-methylcyclopropylmethoxy)phenyl isocyanate was added dropwise, with stirring. The solution was stripped for 2 hours at room temperature, then washed with water, dried, and the solvent stripped off to yield 6.4 g of a liquid. The structure of the product was confirmed by infrared (ir), nuclear magnetic resonance (nmr) and mass spectroscopy (ms).

EXAMPLE 2

Preparation of
N-[2-(methylcarbamyloxy)ethyl]-N-methyl-N'-[3-(2,2-dichloro-1-methylcyclopropyl)methoxy]phenyl urea (Compound 3)

A solution of 3.82 g (0.011 mole) of Compound 1 in 15 ml methylene chloride was prepared. There was added 1 ml of methyl isocyanate and a catalytic amount of triethylamine. The mixture was stirred at room temperature for 2 hours, then washed with water, dried, and the solvent stripped off to yield 4.4 g of a glass. The structure of the product was confirmed by ir, nmr, and ms.

EXAMPLE 3

Preparation of
N-(2-chloroethyl)-N-methyl-N'-[3-(2,2-dichloro-1-methylcyclopropyl)methoxy]phenyl urea (Compound 8)

A solution was prepared by dissolving 3.81 g (0.014 mole) 3-(2',2'-dichloro-1'-methylcyclopropylmethoxy)-phenyl isocyanate and 1.82 g (0.014 mole) 2-chloroethyl methyl amine hydrochloride in 20 ml methylene chloride. There was added 1.52 g triethylamine. The mixture was stirred for 12 hours at room temperature, washed with dilute hydrochloric acid, dried and the solvent stripped off to yield 3.1 g of a solid, m.p. 89°–92° C. The structure of the product was confirmed by ir, nmr, and ms.

The following Table I contains a list of representative compounds of the present invention. Structures of all compounds were confirmed by ir, nmr, and ms.

TABLE I $$\text{structure with X, Y, CH}_3\text{, CH}_2\text{O-phenyl-NHC(O)N(CH}_3\text{)(CH}_2\text{)}_n\text{R}$$

| Compound No. | X | Y | n | R | m.p., °C. or $n_D^{30}$ |
|---|---|---|---|---|---|
| 1 | Cl | Cl | 2 | OH | 1.5534 |
| 2 | Cl | Cl | 2 | O—CH(CH$_3$)OC$_2$H$_5$ | 1.5270 |
| 3 | Cl | Cl | 2 | OC(O)NHCH$_3$ | glass |
| 4 | Cl | Cl | 2 | OC(O)NHC$_6$H$_5$ | glass |
| 5 | Cl | Cl | 2 | OC(O)CH$_2$Cl | 1.5460 |
| 6 | Cl | Cl | 1 | CN | glass |
| 7 | Cl | Cl | 2 | CN | glass |
| 8 | Cl | Cl | 2 | Cl | 89–92° C. |
| 9 | Cl | Cl | 1 | S—i-C$_3$H$_7$ | 1.5596 |
| 10 | Cl | Cl | 2 | piperidin-1-yl | 1.5748 |
| 11 | Cl | Cl | 1 | C$_6$H$_5$ | 93–95° C. |
| 12 | Cl | F | 1 | C$_6$H$_5$ | waxy solid |
| 13 | Cl | F | 2 | Cl | glass |
| 14 | Cl | F | 1 | S—i-C$_3$H$_7$ | glass |
| 15 | Cl | F | 2 | piperidin-1-yl | glass |
| 16 | Cl | F | 2 | CN | waxy solid |

The compounds listed in the foregoing Table I were tested for herbicidal activity as follows:

(a) Pre-emergence Herbicide Screening Test

The compounds were variously tested as pre-emergence herbicides agaist hairy crabgrass (*Digitaria sanguinalis*), foxtail (*Setaria spp.*), watergrass (*Echinochloa crusgalli*), red oat, (*Avena sativa*), wild oat (*Avena fatua*), redroot pigweed (*Amaranthus retroflexus*), Indian mustard (*Brassica juncea*), annual morningglory (*Ipomoea purpurea*), velvetleaf (*Abutilon theophrasti*), and curly dock (*Rumex crispus*). The rate of application was 2 lb/acre (2.25 kg/ha). No activity was demonstrated in these tests.

(b) Post-emergence Herbicidal Evaluation

Flats were filled with 4 pounds of sandy loam soil containing 75 ppm cis-N-[(trichloromethyl)thio]-4-cyclohexene-1,2-dicarboximide and 150 ppm 17-17-17 fertilizer. The moisture content was about 9%. The soil was leveled and row markers used to impress seven rows across the width of the flat. Full rows of foxtail (*Setaria* spp.), watergrass (*Echinochloa crusagalli*), wild oat (*Avena fatua*), Indian mustard (*Brassica juncea*), curly dock (*Rumex crispus*), and pigweed (*Amaranthus retroflexus*) and, in some tests, annual morningglory (*Ipomoea purpurea*) and velvetleaf (*Abutilon theophrasti*) were planted thick enough so that several seedlings emerged per inch of row. The flats were placed in a greenhouse at 70°–85° F. and watered by sprinkling. Eight to twelve days after planting, the flats were sprayed at a rate of 80 gallons of solution per acre. The compound was applied at the rate of 2 lb/acre (2.25 kg/ha).

The spray solution was made up by weighing about 300 mg of the compound into a 120 ml wide-mouth bottle, dissolving it in 50 ml of acetone containing 1% polyoxyethylene sorbitan monolaurate emulsifier and then diluting to 100 ml with water. Additional solvents were used, up to 5 ml, if needed to dissolve the compound.

The flats were returned to the greenhouse after spraying and watered daily without wetting the foliage for three days. Three weeks after treatment, the degree of weed control was estimated and recorded as percentage control compared to the growth of the same species in an untreated check flat of the same age.

The percent control is based on the total injury to the plants due to all factors including inhibited germination, killing of the plant tissue after emergence, stunting, malformation, chlorosis and other types of injury. The control ratings vary from 0 to 100%, where 0 represents no effect with growth equal to the untreated control, and 100 represents complete kill.

The results of these tests are given in the following Table II, in terms of average control of grasses (watergrass, wild oat, foxtail) and broadleaf weeds (for Compounds 1–7: mustard, curly dock and pigweed; Compunds 8–11: mustard, curly dock, pigweed and morningglory; and Compounds 12–16: mustard, pigweed, morningglory and velvetleaf).

TABLE II

| Post-Emergence Control (rate: 2 lb/acre) | | |
| --- | --- | --- |
| Compound No. | Grasses | Broadleaf Weeds |
| 1 | 50 | 100 |
| 2 | 50 | 100 |
| 3 | 0 | 100 |
| 4 | 7 | 73 |
| 5 | 50 | 100 |
| 6 | 20 | 26 |
| 7 | 30 | 86 |
| 8 | 0 | 47 |
| 9 | 23 | 90 |
| 10 | 0 | 67 |
| 11 | 0 | 52 |
| 12 | 0 | 36 |
| 13 | 0 | 45 |
| 14 | 0 | 85 |
| 15 | 0 | 62 |
| 16 | 0 | 87 |

Similar post-emergence tests of Compounds 12–16 were performed using yellow nutsedge (*Cyperus esculentus*). None of these compounds controlled this weed.

Post-flood, Post-emergence Valuation with Paddy Rice

Tubs were filled to a depth of 2 inches with loamy sand soil pretreated with 50 ppm of the fungicide used above and 18-18-18 fertilizer. One pint of soil was removed, the resulting soil was leveled and five rows impressed. There were planted tubers of yellow nutsedge (YN) (*Cyperus esculentus*) and seeds of annual morningglory (MG) (*Ipomoea purpurea*), sesbania (SES) (*Sesbania spp.*), and two varieties of rice (*Oriza sativa*): M-9 and Star Bonnett (SBR). The pint of soil was used to cover the seeds and tubers to a depth of 0.5 inches. The tubs were placed in a greenhouse and irrigated by sprinkling as necessary to keep the soil moist. Three days later another row was impressed 0.5 inches deep and seeds of watergrass (WG) (*Echinochloa crusgalli*) planted and covered with soil. Seven to ten days after the original seeding the soil was covered with 2 inches of water. Test compounds were applied by pipetting into the water a stock solution of the compound dissolved in 20 ml acetone various at levels proportionate to 0.125, 0.25, 0.5, 1, 2, and 4 lb/acre (0.145, 0.28, 0.56, 1.12, 2.24 and 4.48 kg/ha).

Three weeks after application the plant species were rated visually as percent control from 0 to 100%, with 0% representing no injury and 100% complete kill, as compared to an untreated check plot. The results are shown in the following Table III.

TABLE III

| | Post-emergence, post-flood control | | | | | |
| --- | --- | --- | --- | --- | --- | --- |
| Compound No. | Rate (lb/acre) | MG | SES | YN | WG | SBR | M-9R |
| 2 | 0.125 | 0 | 25 | 0 | 10 | 0 | 0 |
| | 0.25 | 0 | 95 | 0 | 10 | 0 | 0 |
| | 0.5 | 0 | 100 | 0 | 95 | 25 | 10 |
| | 1.0 | 100 | 100 | 0 | 100 | 30 | 25 |
| | 2.0 | 100 | 100 | 0 | 100 | 95 | 75 |
| 3 | 0.5 | 0 | 0 | 0 | 0 | 0 | 0 |
| | 1.0 | 100 | 100 | 0 | 25 | 0 | 0 |
| | 2.0 | 100 | 100 | 0 | 95 | 35 | 20 |
| 5 | 0.25 | 0 | 0 | 0 | 0 | 25 | 10 |
| | 0.5 | 100 | 100 | 0 | 65 | 50 | 10 |
| | 1.0 | 100 | 100 | 0 | 75 | 75 | 25 |
| | 2.0 | 100 | 100 | 0 | 95 | 75 | 25 |
| 6 | 0.5 | 0 | 50 | 0 | 0 | 0 | 0 |
| | 1 | 0 | 75 | 0 | 0 | 0 | 0 |
| | 2 | 100 | 75 | 0 | 90 | 0 | 0 |
| | 4 | 100 | 100 | 0 | 95 | 25 | 10 |
| 7 | 0.5 | 0 | 0 | 0 | 0 | 0 | 0 |
| | 1 | 0 | 0 | 0 | 0 | 0 | 0 |
| | 2 | 100 | 100 | 0 | 85 | 0 | 0 |
| | 4 | 100 | 100 | 0 | 95 | 25 | 25 |
| 8 | 1.0 | 0 | 0 | 0 | 0 | 0 | 0 |
| | 2.0 | 100 | 100 | 0 | 85 | 0 | 0 |
| | 4.0 | 100 | 100 | 0 | 90 | 25 | 25 |
| 9 | 0.25 | 0 | 0 | 0 | 0 | 0 | 0 |
| | 0.5 | 100 | 100 | 0 | 0 | 0 | 0 |
| | 1.0 | 100 | 100 | 0 | 0 | 0 | 0 |
| | 2.0 | 100 | 100 | 0 | 60 | 60 | 60 |
| 10 | 2.0 | 0 | 0 | 0 | 0 | 0 | 0 |
| | 4.0 | 90 | 90 | 10 | 20 | 0 | 0 |
| 11 | 0.5 | 100 | 0 | 0 | 0 | 0 | 0 |
| | 1.0 | 100 | — | 0 | 0 | 0 | 0 |
| | 2.0 | 100 | 90 | 0 | 0 | 0 | 0 |
| | 4.0 | 100 | 90 | 0 | 20 | 0 | 0 |
| 14 | 0.25 | 0 | 0 | 0 | 0 | 0 | 0 |
| | 0.5 | 0 | 100 | 0 | 25 | 0 | 0 |
| | 1.0 | 0 | 100 | 0 | 50 | 50 | 50 |
| | 2.0 | 100 | 100 | 0 | 90 | 90 | 75 |
| | 4.0 | 100 | 100 | 0 | 100 | 100 | 90 |

In practice, a pure compound can be used as a herbicide. However, in general, the compounds are first formulated with one or more inert carriers or diluents suitable for herbicidal use, before being applied.

The compositions or formulations, including a compound as described herein, may take and be used in any one of a number of solid or liquid forms. Examples of solid forms are dusts, granules, tablets, powders, and the like. Examples of liquid forms are emulsions, solutions, suspensions, emulsifiable concentrates, flowables, and pastes. Such compositions may contain, in addition to the active compound or compounds, various carriers or diluents; surface active agents (wetting agents, dispersing agents and/or emulsifying agents); solvents (water or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons with an emulsifying agent. To obtain suspensions or emulsions in water, wetting agents are also added.

It is possible to use highly concentrated liquid compositions containing up to about 95% by weight of the active compound, or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes, —20 to 90% active compound; oil suspensions, emulsions, solutions and emulsifiable concentrates —5 to 90% active compound; aqueous suspensions —10 to 50% active compound; dusts and powders —1 to 25% active compound; granules and pellets —1 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more active compounds of the type mentioned herein as well as other active pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount may be applied to the plant or locus to be controlled in any conventional manner. Thus, powders and various liquid compositions containing the active compound can be applied by the use of power dusters, boom and hand sprayers and spray dusters or applied from airplanes as dusts or sprays. When applied in the latter method, they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

What is claimed is:

1. A compound having the formula

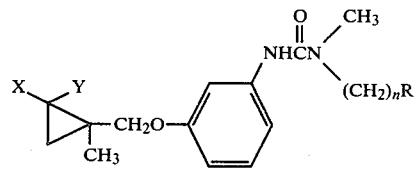

in which X and Y are halogen; R is cyano, halogen, thio-$C_1$-$C_4$ alkyl, phenyl, pyridyl, hydroxy, or $OR_1$; $R_1$ is $C_1$-$C_4$ alkyl, $C_1$-$C_4$ mono- or di-alkylcarbamyl, $C_2$-$C_6$ alkoxyalkyl, phenylcarbamyl, $C_1$-$C_6$ alkanoyl or $C_1$-$C_6$ haloalkanoyl; and n is: (a) 1 or 2 if R is thioalkyl, cyano or phenyl; and (b) 2 if R is otherwise as defined.

2. A compound according to claim 1 in which X and Y are both chloro.

3. A compound according to claim 1 in which X is chloro and Y is fluoro.

4. A compound according to claim 1 in which n is 2.

5. A compound according to claim 1 in which X and Y are both chloro, n is 2 and R is hydroxy.

6. A compound according to claim 1 in which X and Y are both chloro, n is 2 and R is (1-ethoxy)ethoxy.

7. A compound according to claim 1 in which X and Y are both chloro, n is 2 and R is methylcarbamyloxy.

8. A compound according to claim 1 in which X and Y are both chloro, n is 2 and R is phenylcarbamyloxy.

9. A compound according to claim 1 in which X and Y are both chloro, n is 2 and R is chloroacetoxy.

10. A compound according to claim 1 in which X and Y are both chloro, n is 1 and R is cyano.

11. A compound according to claim 1 in which X and Y are both chloro, n is 2 and R is cyano.

12. A compound according to claim 1 in which X, Y and R are all chloro and n is 2.

13. A compound according to claim 1 in which X and Y are both chloro, R is isopropylthio and n is 1.

14. A compound according to claim 1 in which X and Y are both chloro, R is 2-pyridyl and n is 2.

15. A compound according to claim 1 in which X and Y are both chloro, R is phenyl and n is 1.

16. A compound according to claim 1 in which X is chloro, Y is fluoro, R is phenyl and n is 1.

17. A compound according to claim 1 in which X is chloro, Y is fluoro, R is chloro and n is 2.

18. A compound according to claim 1 in which X is chloro, Y is fluoro, R is isopropylthio and n is 1.

19. A compound according to claim 1 in which X is chloro, Y is fluoro, R is 2-pyridyl and n is 1.

20. A compound according to claim 1 in which X is chloro, Y is fluoro, R is cyano and n is 2.

21. A method of controlling undesirable vegetation comprising applying to the vegetation or the locus thereof a herbicidally effective amount of a compound having the formula

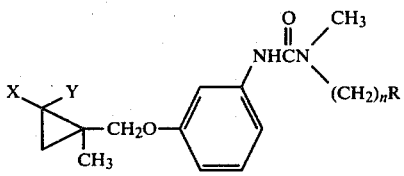

in which X and Y are halogen; R is cyano, halogen, thio-$C_1$-$C_4$ alkyl, phenyl, pyridyl, hydroxy, or $OR_1$; $R_1$ is $C_1$-$C_4$ alkyl, $C_1$-$C_4$ mono- or di-alkylcarbamyl, $C_2$-$C_6$ alkoxyalkyl, phenylcarbamyl, $C_1$-$C_6$ alkanoyl, or $C_1$-$C_6$ haloalkanoyl; and n is: (a) 1 or 2 if R is thioalkyl, cyano or phenyl; and (b) 2 if R is otherwise as defined.

22. A method according to claim 21 in which the compound is applied to control undesirable broadleaf vegetation.

23. A method according to claim 21 in which the compound is applied to the vegetation or the locus thereof subsequent to the emergence of vegetation at the locus.

24. A method according to claim 21 in which X and Y are both chloro.

25. A method according to claim 21 in which n is 2.

26. A method according to claim 21 in which X and Y are both chloro, R is hydroxy and n is 2.

27. A method according to claim 21 in which X and Y are both chloro, R is (1-ethoxy)ethoxy and n is 2.

28. A method according to claim 21 in which X and Y are both chloro, R is methylcarbamyloxy and n is 2.

29. A method according to claim 21 in which X and Y are both chloro, R is chloroacetoxy and n is 2.

30. A method according to claim 21 in which X and Y are both chloro, R is cyano and n is 2.

31. A method according to claim 21 in which X and Y are both chloro, R is isopropylthio and n is 1.

32. A method according to claim 21 in which X and Y are both chloro, R is cyano and n is 1.

33. A method according to claim 21 in which X is chloro, Y is fluoro, R is isopropylthio and n is 1.

34. A method according to claim 21 in which X is chloro, Y is fluoro, R is cyano and n is 2.

35. A herbicidal composition comprising:
(a) a herbicidally effective amount of a compound having the formula

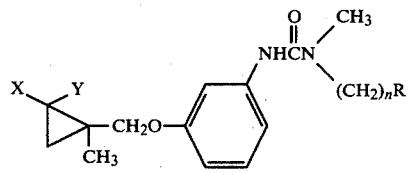

in which X and Y are halogen; R is cyano, halogen, thio-$C_1$-$C_4$ alkyl, phenyl, pyridyl, hydroxy, or $OR_1$; $R_1$ is $C_1$-$C_4$ alkyl, $C_1$-$C_4$ mono- or di-alkylcarbamyl, $C_2$-$C_6$ alkoxyalkyl, phenylcarbamyl, $C_1$-$C_6$ alkanoyl, or $C_1$-$C_6$ haloalkanoyl; and n is: (a) 1 or 2 if R is thioalkyl, cyano or phenyl; and (b) 2 if R is otherwise as defined; and
(b) a herbicidally suitable inert carrier or diluent.

* * * * *

UNITED STATES PATENT AND TRADEMARK OFFICE
CERTIFICATE OF CORRECTION

PATENT NO. : 4,361,438
DATED : November 30, 1982
INVENTOR(S) : Raymond A. Felix

It is certified that error appears in the above-identified patent and that said Letters Patent is hereby corrected as shown below:

In Column 4, line 12, Compound No. 10, the definition for "R" should read,

---  ---

In Column 4, line 23, Compound No. 15, the definition for "R" should read,

--- 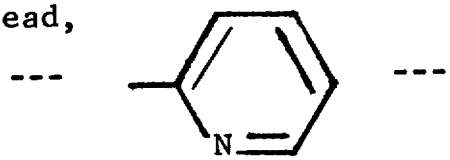 ---

Signed and Sealed this

Twenty-ninth Day of May 1984

[SEAL]

Attest:

GERALD J. MOSSINGHOFF

Attesting Officer  Commissioner of Patents and Trademarks